(12) United States Patent
Batiste et al.

(10) Patent No.: US 9,603,695 B2
(45) Date of Patent: Mar. 28, 2017

(54) BYPASS VASCULAR GRAFT

(75) Inventors: Stanley Batiste, Granite Bay, CA (US); Steven Achstein, Roseville, CA (US)

(73) Assignee: Stanley Batiste, Granite Bay, CA (US)

( * ) Notice: Subject to any disclaimer, the term of this patent is extended or adjusted under 35 U.S.C. 154(b) by 898 days.

(21) Appl. No.: 13/212,129

(22) Filed: Aug. 17, 2011

(65) Prior Publication Data
US 2012/0022428 A1 Jan. 26, 2012

Related U.S. Application Data

(63) Continuation-in-part of application No. 11/977,953, filed on Oct. 26, 2007.

(60) Provisional application No. 60/873,788, filed on Dec. 7, 2006.

(51) Int. Cl.
*A61M 5/00* (2006.01)
*A61F 2/06* (2013.01)

(52) U.S. Cl.
CPC ............... *A61F 2/06* (2013.01); *A61F 2/064* (2013.01)

(58) Field of Classification Search
CPC ....................................................... A61M 5/00
USPC ....................................................... 623/1.24
See application file for complete search history.

(56) References Cited

U.S. PATENT DOCUMENTS

| | | |
|---|---|---|
| 5,197,976 A | 3/1993 | Herweck et al. |
| 5,662,711 A | 9/1997 | Douglas |
| 6,338,724 B1 | 1/2002 | Dossa |
| 6,589,278 B1 | 7/2003 | Harris et al. |
| 7,105,020 B2 | 9/2006 | Greenberg et al. |
| 7,128,750 B1 | 10/2006 | Stergiopulos |

*Primary Examiner* — Matthew Schall
(74) *Attorney, Agent, or Firm* — Weide & Miller, Ltd.

(57) ABSTRACT

A vascular connector configured to bypass an occluded vessel comprises a primary graft stem and a venous outflow stem. In general, the primary graft stem accepts a blood flow from an occluded vessel to bypass the occlusion. The venous outflow stem may extend from a wall of the primary graft stem and divert a portion of the blood flow to a native vein or other vessel of the vascular system. This configuration is beneficial in ensuring adequate blood flow at the vascular connector to inhibit the formation of clots and to extend the patency of the vascular connector.

10 Claims, 7 Drawing Sheets

BYPASS VASCULAR GRAFT

CROSS-REFERENCE TO RELATED APPLICATIONS

This application is a continuation-in-part of U.S. patent application Ser. No. 11/977,953, filed Oct. 26, 2007, which claims priority to U.S. Provisional Patent Application No. 60/873,788 filed Dec. 7, 2006.

BACKGROUND OF THE INVENTION

1. Field of the Invention

The present invention relates to vascular bypass grafts and, in particular, to surgically implanted grafts which increase blood flow and reduce clotting.

2. Related Art

Vascular disease is a leading cause of morbidity and mortality in the United States and throughout the world. The causes of vascular disease include diabetes, hypertension, renal failure, and smoking as well as many other etiologies. Vascular disease can affect any blood vessel in the body and commonly involves the coronary arteries, carotid arteries and the arteries of the lower extremities. The disease is caused by cholesterol, plaque, and calcium deposits which cause vascular wall thickening. Vascular wall thickening occludes the afflicted vessels by narrowing them, which reduces or in some cases, completely blocks blood flow.

Vascular disease is currently treated in several different ways. Patients may engage lifestyle changes, changes to diet and exercise, and medical therapies such as cholesterol lowering drugs. However, for some patients, these non-invasive treatments are insufficient and surgical or invasive intervention such as bypass surgery or angioplasty are necessary.

A patient undergoing bypass surgery has a bypass graft, surgically implanted. The bypass graft provides a substitute route for blood flow to bypass an to occluded region. The bypass graft is a tube structure with two ends. One end attaches on one end before the region of vascular occlusion, and on the other end to the patient's vascular system downstream of the occlusion. In this manner, the bypass graft improves the patient's blood flow around the occlusion.

The majority of bypass grafts function well over time, however, in a significant number of patients the bypass grafts themselves become occluded. Where a bypass graft becomes occluded, the patient must undergo another surgery to place a second graft or to repair the original graft.

As a result, there is a need in the art for a bypass graft that can provide a route for blood flow while preventing occlusion which leads to graft failure. The description herein enables such a bypass graft as well as a method of implanting the bypass graft.

BRIEF SUMMARY OF THE INVENTION

A vascular connector for bypassing an occluded vessel, such as a vein or artery, is disclosed herein. The vascular connector has features which help ensure an adequate blood flow through the connector after implantation in a patient's vascular system. This is highly beneficial in that it greatly reduces, if not eliminates, the risk of clots forming within the connector and, accordingly, improves graft patency.

The vascular connector may have various configurations. For example, in one embodiment a vascular connector may comprise a primary graft stem fabricated from a substantially hollow member. The primary graft stem may have a first end and a second end to allow blood flow from a first blood vessel through the primary graft stem. It is noted that one end of the primary graft stem may be tapered such as to increase blood pressure at the tapered end. A venous outflow stem fabricated from a substantially hollow member may extend outward from an opening in the primary graft stem to divert a portion of the blood flow from the primary graft stem to a second blood vessel.

One or more ridges may be at one or both ends of the primary graft stem. Similarly, one or more ridges may be at an outflow end of the venous outflow stem. It is noted that the venous outflow stem may extend beyond the first end of the primary graft stem.

In another embodiment, the vascular connector may comprise a primary stem fabricated from a substantially hollow structure and configured to accept a blood flow from a narrowed vessel to bypass the narrowed vessel. A secondary stem fabricated from a substantially hollow structure having a narrower diameter than the primary stem may extend from a wall of the primary stem. The secondary stem may be configured to accept a portion of the blood flow within the primary stem, and divert the portion of blood flow to another vessel.

Similar to above, at least one end of the primary stem may be tapered. It is noted that the secondary stem may be integrally formed with the primary stem or alternatively be a separate structure attached to the primary stem. A tubular venous outflow limb may be to an outflow end of the secondary stem. The secondary stem may extend from a central portion of the primary stem. Alternatively, the secondary stem extends from a wall of the primary stem at one end of the primary stem. Various methods of bypassing an occluded vessel are disclosed herein as well. For example, a method of bypassing blood flow through a vessel having an occlusion includes providing a vascular connector having a primary stem and a narrower secondary stem extending from an opening in a wall of the primary stem, connecting a first end of the primary stem to the vessel upstream of the occlusion in the vessel, and connecting a second end of the primary stem to a vascular system downstream of the occlusion in the vessel. An outflow end of the secondary stem may then be connected to another vessel of the vascular system. It is noted that a venous outflow limb may be connected to the outflow end of the secondary stem. The venous outflow limb may connect the secondary stem to the other vessel of the vascular system.

It is noted that connecting the vessel to the first end of the primary stem may comprise inserting a ridged first end of the primary stem into an end of the vessel. It is also noted that the vessel may be an artery of the vascular system while the other vessel is a vein of the vascular system.

Further objects, features, and advantages of the present invention over the prior art will become apparent from the detailed description of the drawings which follows, when considered with the attached figures.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE PREFERRED EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The primary reason for the formation of blood clots in a bypass graft is that the blood flow through the graft is of such low velocity that blood clotting mechanisms are triggered. Regions of low velocity blood flow are common in the body's smaller vessels such as veins and capillaries. Low velocity regions are also found in the transitions between larger vessels, such as arteries, to smaller ones, such as veins or capillaries because the reduction in size reduces flow capacity and thus blood flow velocity is also reduced. Thus, if a bypass graft is attached to a small vessel at its outflow end or in a region of low velocity blood flow, only a small amount of blood at low velocity flows through the graft creating circumstances where blood clots may form within the graft. This will cause occlusion of the graft and eventual graft failure.

In general, a vascular bypass graft which improves blood flow in occluded vascular regions and is itself resistant to occlusion by blood clots is disclosed. The vascular bypass graft disclosed herein has several advantages over known bypass grafts. It maintains a high blood flow velocity in conditions where there would otherwise be a low flow rate through the graft, such as where outflow from the distal vascular bypass graft end is low or reduced. Currently known grafts will not stay un-occluded in these conditions because the slow flow through the graft allows blood clots to develop and occlude the graft eventually rendering it non-functional.

Another advantage of the method and apparatus described herein is that the amount of return flow provided through the venous outflow limb is adjustable. In this way, the vascular bypass graft can be custom configured for a particular patient and/or medical application. One aspect of this adjustability is that it is non-invasive and thus allows modification of the amount of blood flow through the vascular bypass graft in response to the new medical conditions or other factors without the need for further surgery.

Figure 1:
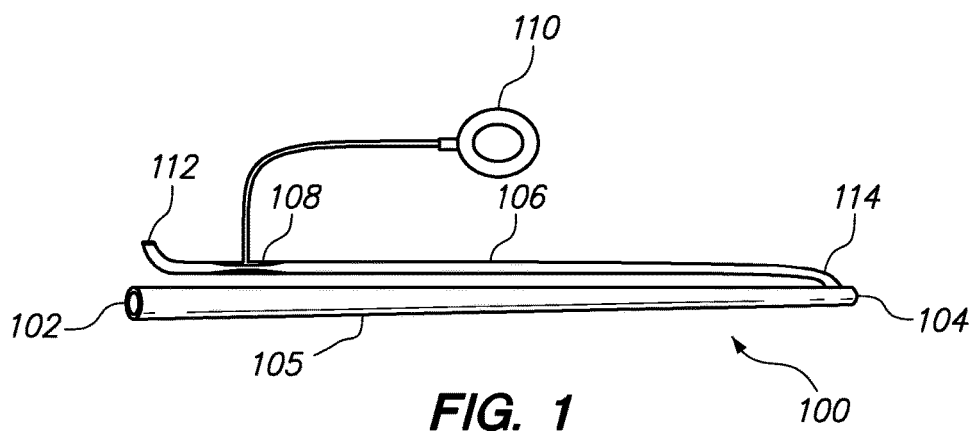
FIG. 1 illustrates an exemplary embodiment of a vascular bypass graft.

Referring now to the drawings, FIG. 1 illustrates an improved vascular bypass graft 100. The vascular bypass graft 100 has a primary member/graft 105, a proximal/first vascular bypass end 102, a distal/second vascular bypass end 104, a venous outflow limb 106, a stenosis restrictor 108, and an optional restrictor controller 110. The venous outflow limb 106 or secondary member has a proximal/first venous end 112 and a distal/second venous end 114. The distal venous end 114 attaches to or is integrally formed adjacent to the distal vascular bypass end 104 such that a flow path is provided that facilitates fluid transmission from the primary graft 105 to the venous outflow limb 106. The vascular bypass graft 100 or any portion thereof can be made in any length to accommodate the need for various vascular systems.

The primary graft 105 is generally a flexible hollow elongate member comprising structure and dimensional configurations to facilitate fluid transmission from the proximal vascular bypass end 102 to the distal vascular bypass end 104. The venous outflow limb 106 is generally a flexible hollow elongate member structured and dimensionally configured to facilitate fluid transmission from the distal venous end 114 to the proximal venous end 112. In one embodiment, the primary graft 105 and venous outflow limb 106 are fabricated from a material that is suitable for surgical implantation into a living organism. The material should be selected for compatibility with living tissue. Such materials include but are not limited to prosthetic polytetraflouroethylen (PTFE) and polyethylene tetraphthlate (Dacron).

In one embodiment, when implanted, the vascular bypass graft 100 is attached to a patient's vascular system at the proximal vascular bypass end 102, the distal vascular bypass end 104, and the proximal venous end 112. In one embodiment, the vascular bypass graft is implanted such that blood flows through the primary graft 105 from the proximal vascular bypass end 102 to the distal vascular bypass end 104. The proximal venous end 112 of the venous outflow limb 106 may be attached to a blood vessel of lower pressure. This attachment of the proximal venous end 112 to a blood vessel of lower pressure ensures that at least a portion of blood in the primary graft 105 flows through the venous outflow limb 106 because fluids, including blood, will naturally flow to a region of lower relative pressure.

The venous outflow limb 106 allows the primary graft 105 to maintain blood flow velocity sufficient to prevent clotting even when the flow velocity would ordinarily be low due to minimal outflow through the distal vascular bypass end 104. Blood flow travels through the primary graft 105 from the proximate vascular bypass end 102 to the distal vascular bypass end 104 with at least a portion of the blood flow diverted through the venous outflow limb 106. This portion of diverted blood flow allows the blood to circulate through the vascular bypass graft 100 at a flow velocity sufficient to prevent clotting even where the patient's vascular system at the distal vascular bypass end 104 has a low blood flow capacity. Thus, the patient's vascular system at the distal vascular bypass end 104 receives its necessary blood flow while the excess blood flow is circulated through the venous outflow limb 106 to a blood vessel of lower pressure to prevent clotting within the vascular bypass graft 100.

The stenosis restrictor 108 controls the amount of blood flow through the venous outflow limb 106 by restricting blood flow through the venous outflow limb 106. The stenosis restrictor 108 can completely restrict (i.e. block) blood flow as well. This control is desirable because it allows the vascular bypass graft 100 to be configured to the needs of each particular patient at a particular time. More specifically, the stenosis restrictor 108 can increase or decrease blood pressure at the distal vascular bypass end by increasing or decreasing the amount of blood flowing through the venous outflow limb 106. Thus, the stenosis restrictor 108 could decrease blood flow through the venous outflow limb to increase blood pressure, for example, to outer extremities or anytime the body requires it such as during physical activity. Conversely, the stenosis restrictor 108 could increase blood flow through the venous outflow limb to decrease blood pressure at the distal vascular bypass end 104 and increase anti-clotting circulation through the vascular bypass graft 100 when such increased blood pressure is not necessary.

In one embodiment, a desired flow condition provides sufficient flow through the primary graft 105 to prevent clotting while still maintaining sufficient pressure at the distal vascular bypass end 104. By selecting the proper stenosis restrictor 108 setting, the pressure and flow rate may be optimized.

The stenosis restrictor 108 may comprise various configurations, devices, or systems that restrict blood flow to achieve operation as described herein including but not limited to balloon or other inflatable devices or other pneumatic or hydraulic systems. In addition, the stenosis restrictor 108 may operate in conjunction with a restrictor controller 110 to variably control the amount of blood flow restriction.

In one embodiment the stenosis restrictor 108 comprises a balloon. In this embodiment, the restrictor controller 110 comprises a pneumatic or hydraulic device for inflating and deflating the balloon to thereby adjust the amount of blood flow restriction. The restrictor controller 110 as a pneumatic or hydraulic device may be configured as a gas or liquid reservoir connected to the stenosis restrictor 108. The amount of blood flow restriction can then be varied by altering the volumetric capacity of the restrictor controller 110 to which the stenosis restrictor 108 is linked The degree to which the stenosis restrictor 108 restricts blood flow through the venous outflow limb 106 may be substantially proportional and inverse to the volumetric capacity of the restrictor controller 110 of this embodiment.

Figure 2A:
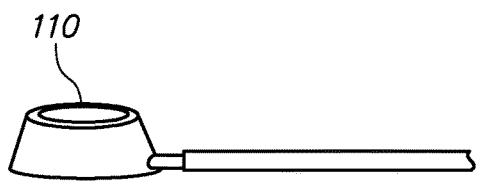
FIG. 2A illustrates a reservoir for a stenosis restrictor of the vascular bypass graft of FIG. 1.
Figure 2B:
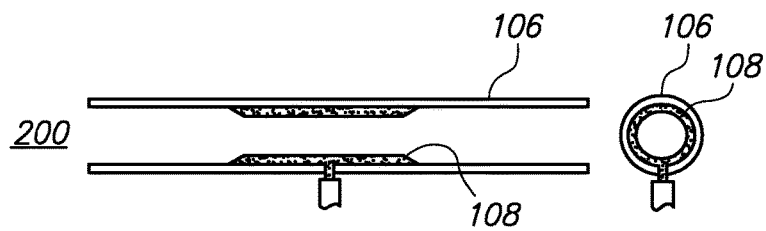
FIG. 2B illustrates a cross-sectional view of a deflated stenosis restrictor of FIG. 1.
Figure 2C:
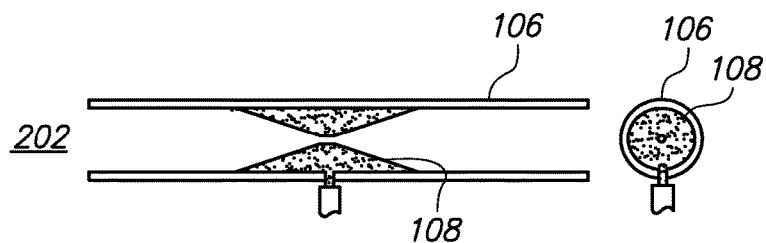
FIG. 2C illustrates a cross-sectional view of an inflated stenosis restrictor of FIG. 1.

The stenosis restrictor 108 and restrictor controller 110 are illustrated in greater detail in FIGS. 2A through 2C. In FIGS. 2B and 2C the stenosis restrictor 108 is shown in both a longitudinal cross-section and a transverse cross-section. Additionally, the stenosis restrictor 108 is depicted in a first deflated state 200 in FIG. 2B and a second inflated state 202 in FIG. 2C. As shown in FIG. 2B, the stenosis restrictor 108 is deflated and provides little resistance to fluid flow within the venous outflow limb 106 thus reducing fluid pressure within the primary graft 105. Conversely, in FIG. 2C, the stenosis restrictor 108 is inflated providing increased resistance to fluid flow within the venous outflow limb 106 thus increasing the overall fluid pressure within the vascular bypass graft.

Figure 3A:
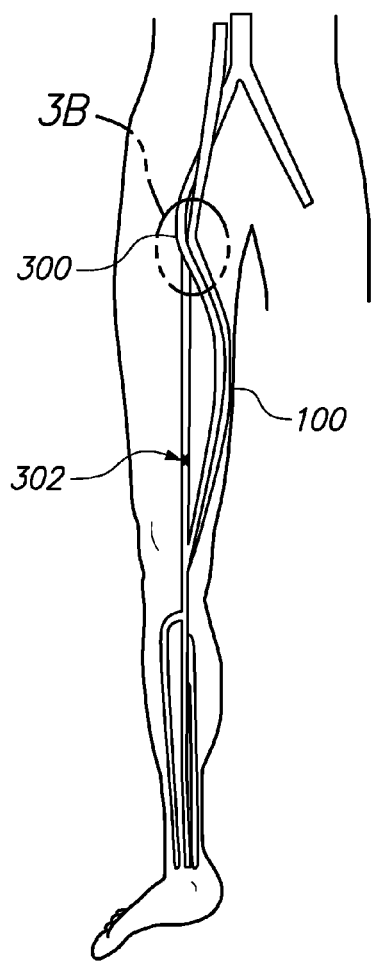
FIG. 3A is a regional view of the proximal connections of the vascular bypass graft of FIG. 1.
Figure 3B:
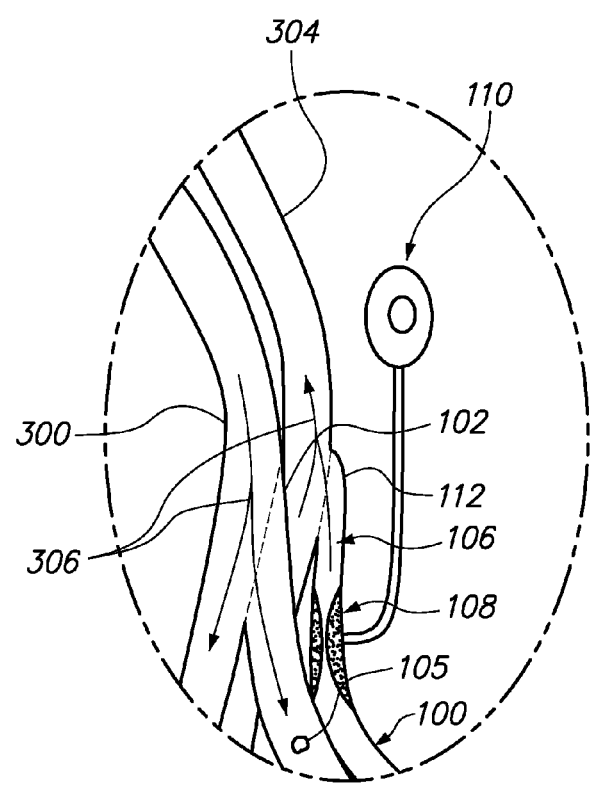
FIG. 3B is an enlarged detail view of the proximal connections of the vascular bypass graft of FIG. 1.

Reference is now made to FIGS. 3A and 3B which illustrate an embodiment of the vascular bypass graft 100 attached to a patient's vascular system. The proximate vascular bypass end 102 of the vascular bypass graft 100 is attached to a patient's artery 300 at a proximate end located upstream from the vascular occlusion 302. This results in blood flow 306 being diverted into the vascular bypass graft 100 from the artery 300. The proximate venous end 112 is attached to a patient's blood vessel 304 of lower pressure, to permit blood flowing through the venous outflow limb 106 to return to the patient's vascular system.

Figure 4A:
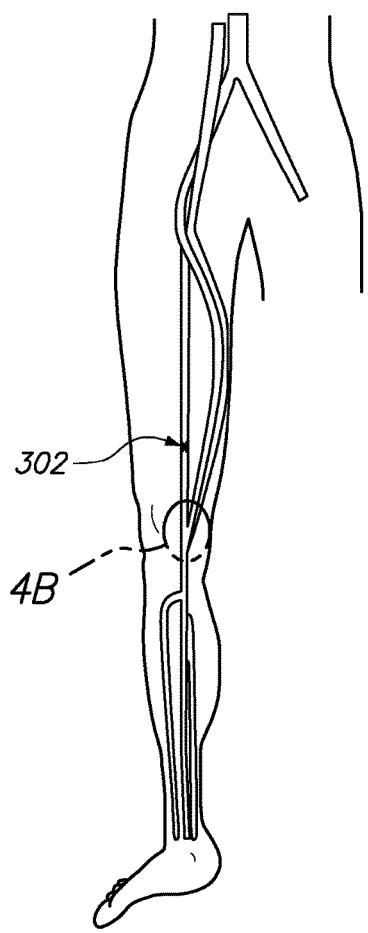
FIG. 4A is a regional view of the distal connections of the vascular bypass graft of FIG. 1.
Figure 4B:
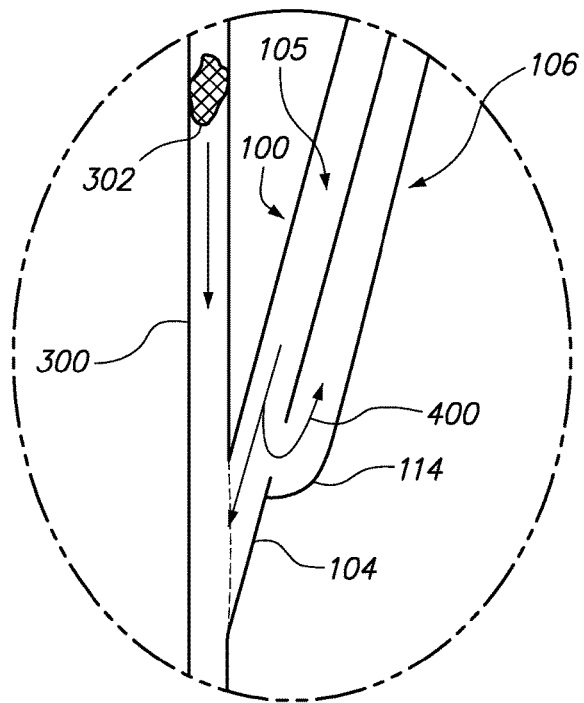
FIG. 4B is an enlarged detail view of the distal connections of the vascular bypass graft of FIG. 1.

FIGS. 4A and 4B illustrate the distal end of the vascular bypass graft 100 attaching to a patient's vascular system. The distal vascular bypass end 104 of the vascular bypass graft 100 is attached to a patient's artery 300 at a distal end located downstream from the vascular occlusion 302. The blood flow that was diverted into the vascular bypass graft 100 from the artery 300 as described above reenters the artery at a location beyond the vascular occlusion thus bypassing the vascular occlusion 302. As seen in FIG. 4B, a portion of the blood flow 400 through the vascular bypass graft's 100 primary graft 105 is diverted into the venous outflow limb 106 through the distal venous end 114 for subsequent return into the patient's vascular system by way of blood vessel 304 as shown in FIG. 3B.

It should be noted that the vascular bypass graft 100 as shown in FIGS. 3A, 3B, 4A, and 4B is shown in a particular vascular configuration. However, the vascular bypass graft 100 is designed to be utilized in any other suitable vascular system including but not limited to the upper extremity, the coronary arterial system and the abdominal, or pelvic vascular system.

Figure 5A:
FIGS. 5A through 5E illustrate a series of alternate embodiments of an vascular bypass graft.
Figure 5B:
Figure 5C:
Figure 5D:
Figure 5E:
Figure 6A:
FIG. 6A illustrates an alternate embodiment of a vascular bypass graft having a flared venous outflow limb.

Several variations of the vascular bypass graft 100 are shown in FIGS. 5B through 5E in comparison to a known standard bypass graft 500 as shown in FIG. 5A. The design of the venous outflow limb may take on various configurations including the side-by-side configuration shown in FIGS. 5B through 5D and cross-section FIG. 6B. In another embodiment, the vascular bypass graft 100 has a unitary construction with the venous outflow limb 106 being integrally formed with the vascular bypass graft 100 as shown in FIGS. 5E, 6A, and cross-section FIG. 6D. In the embodiment shown in FIG. 5B, the vascular bypass graft 100 comprises a long venous outflow limb 502. In another embodiment, the venous outflow limb may be a medium length venous outflow limb 504 as shown in FIG. 5C. In yet another embodiment, a short length venous outflow limb 506 may be configured with the vascular bypass graft 100 as shown in FIG. 5D.

It is contemplated that the various lengths of the venous outflow limbs are selected and implemented as required by the medical circumstances. For example, in one patient, the distal vascular bypass end may be located very close to a patient's vein and a short venous outflow limb 506 would facilitate connection of the venous outflow limb to the native vein in the most efficient manner. In contrast, the distal vascular bypass end may be located far away from a patient's native vein and the use of a long venous outflow limb 502 would be necessary. It is further contemplated that there are many variations with respect to the length of the venous outflow limb and other configurations are possible within the scope of the invention disclosed herein.

In one embodiment, the vascular bypass graft, including its primary graft portion and its venous outflow limb portion, are adjustable, separately or as a whole, such as by a cut-to-length fit during surgery to specially fit the vascular bypass graft to a particular patient.

FIG. 5E shows the embodiment where a venous outflow limb 508 is integrally formed with the vascular bypass graft 100. This integral venous outflow limb 508 makes the vascular bypass graft 100 easier to surgically place because there is primarily only one member to manipulate during the installation of the graft. By combining this venous outflow limb 508 with the primary structure of the vascular bypass graft 100 tangling or damage to this venous outflow limb 508 during surgery is reduced. As with the other embodiments, this venous outflow limb 508 can be made any length, independent of the length of the vascular bypass graft 100. The length of this venous outflow limb 508 also being dependant upon the distance required to extend to the best outflow attachment blood vessel.

Figure 6C:
FIG. 6C illustrates an alternate embodiment of a vascular bypass graft having an integral flared venous outflow limb.
Figure 6B:
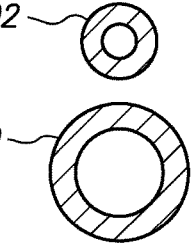
FIG. 6B is a cross-sectional view of the alternate embodiment of FIG. 6A.
Figure 6D:
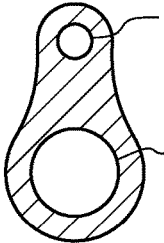
FIG. 6D is a cross-sectional view of the alternate embodiment of FIG. 6C.

In another embodiment, shown in FIGS. 6A and 6C, the venous outflow limb is configured with a flared proximate venous end 600. The flared proximate venous end 600 functions as a fluid diffuser that reduces the exit pressure of blood leaving the proximate venous end prior to re-entry into the patient's vascular system. As a result, the blood flow entering the patient's blood vessel is at a substantially similar pressure which reduces chances of blood clotting, and potential damage to the vascular walls at the re-entry blood vessel. A high pressure differential at the proximate venous end could result in repeated expansion and contraction of the re-entry blood vessel which in turn leads to scarring and thus narrowing of such blood vessel.

Additional embodiments may provide various means for adjusting or controlling the restrictor controller and/or the stenosis restrictor, including various pumps, valves, and devices for adjusting the stenosis restrictor or any other device, which may be dependant on the type of restrictor used. If a balloon-type stenosis restrictor is used, then a deflating/inflating device may be used to control the restriction on blood flow.

Figure 7A:
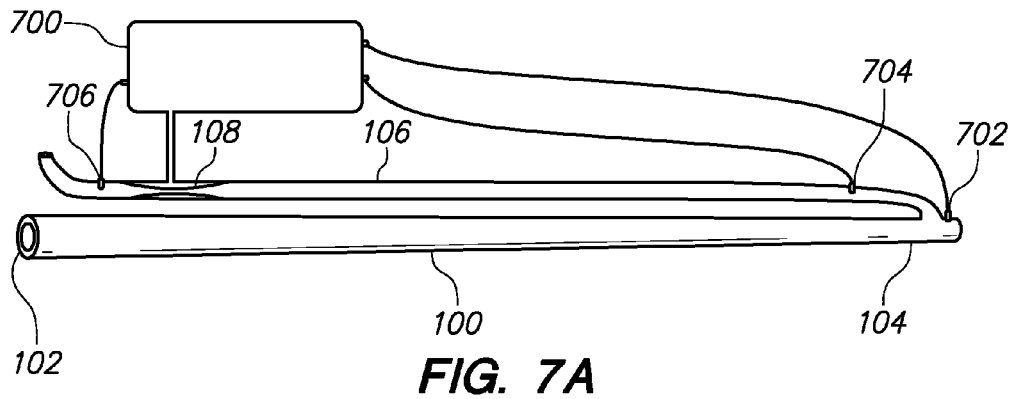
FIG. 7A illustrates an alternate embodiment of a vascular bypass to graft having a controller.

In the embodiment shown in FIG. 7A, a controller 700, which may be electrical, mechanical, or a combination of both, is utilized to control the stenosis restrictor 108. The controller 700 can operate in conjunction with various combinations of graft output sensors 702, venous limb high pressure/flow sensors 704, or venous limb low pressure/flow sensors 706.

These sensors monitor one or more fluid dynamic parameters within the vascular bypass graft and provide this information to the controller 700 via electrical, optical, mechanical or other signaling. Fluid dynamic parameters are data relating to the movement of fluid within the vascular bypass graft such as but not limited to blood flow rate, pressure, or both. Fluid dynamic parameters may also include characteristics of the vascular bypass graft itself such as but not limited to the length and volumetric capacity of various sections of the vascular bypass graft.

Data comprising fluid dynamic parameters may be collected from the sensors in a variety of ways. In one embodiment, some or all the sensors are activated by the controller 700 when the controller requires or requests sensor information. However, in other embodiments, the sensors may continuously provide sensor information which the controller 700 may periodically, continuously, or at any other time collect. The controller may be operatively coupled to the stenosis. The term operatively coupled is defined to mean connected to or in communication with, such as by mechanical, physical electrical, pneumatic, magnetic, radio, or any other means.

Figure 7B:
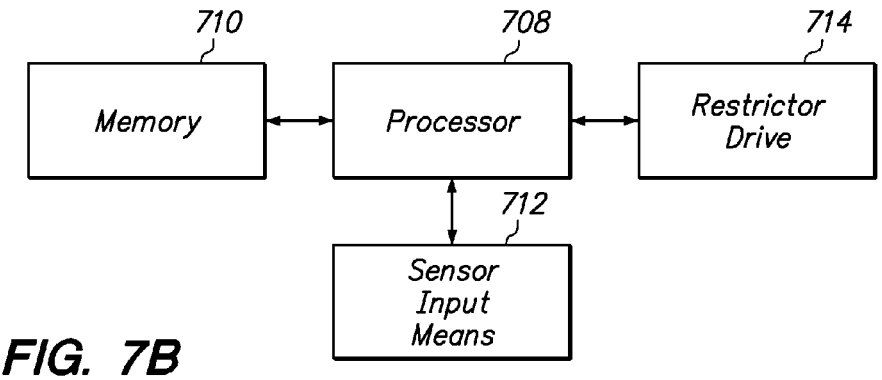
FIG. 7B is a block diagram of an exemplary embodiment for a closed-loop feedback controller of FIG. 7A.

FIG. 7B illustrates internal components for one embodiment of the controller 700. In this embodiment, the controller 700 has a processor 708 with memory 710 for storing machine executable code and sensor information. The machine executable code includes one or more sets of instructions which are interpreted or executed by the processor 708 to accomplish a desired result. In one or more embodiments, the machine executable code may instruct the processor 708 to collect sensor information, perform calculations upon or process the sensor information, and provide an output. This output may be used to control a restrictor driver 714 which controls the stenosis restrictor. The processor 708 may execute or the machine executable code may instruct the processor to use the memory 710 to store and/or retrieve data including but not limited to sensor information, intermediate or final outputs, or additional machine executable code. Communication between the internal components of the controller 700 may be bi-directional.

In one or more embodiments, the processor 708 may base its output or commands to the restrictor driver 714 on a plurality of sensor information collected through sensors connected to a sensor input 712. The controller 700 may be programmed to manually, periodically, or continuously monitor and adjust the performance of the vascular bypass graft based on fluid dynamic parameters such as but not limited to pressure or flow rate or both collected from various sources and sensors. The processor 708 may then adjust the stenosis restrictor accordingly.

For example, the vascular bypass graft 100 illustrated in FIG. 7A may be fitted with one or more of a graft output sensor 702, a venous limb high pressure/flow sensor 704 and/or a venous limb low pressure/flow sensor 706. The information from these sensors is communicated to the controller 700 to form a closed-loop feedback control system for dynamic adjustment stenosis, which in turn controls the flow through the outflow limb, which in turn controls the flow through the vascular bypass graft 100. It is contemplated that the invention may be practiced with additional or fewer sensors 706 depending on the degree of flow control needed for a particular application.

Figure 7C:
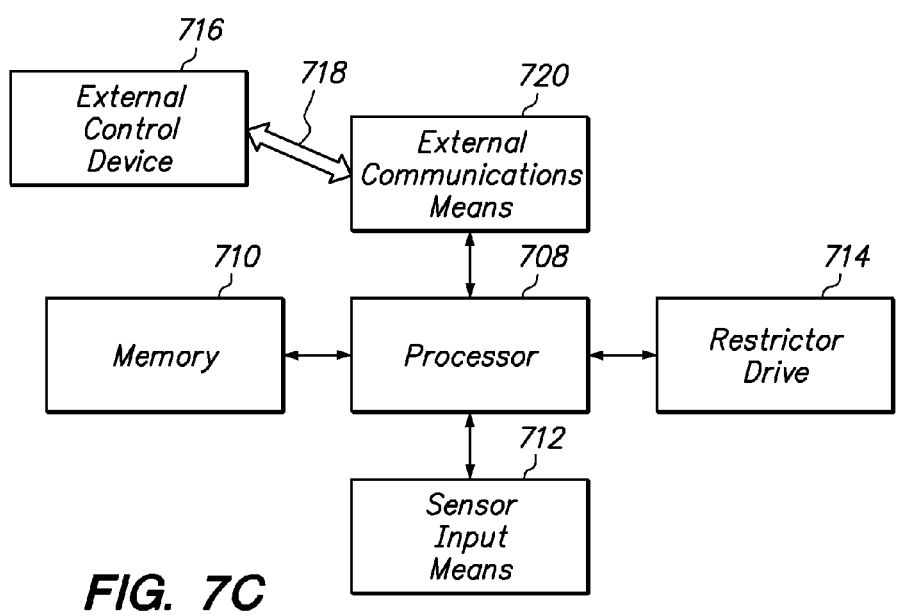
FIG. 7C is a block diagram of an exemplary embodiment for an open-loop feedback controller of FIG. 7A.

In another embodiment shown in FIG. 7C, the controller 700 is configured as an open-loop control system. In this variation, the processor 708 may communicate with an external control device 716. In this embodiment, the processor 708 may receive information from its sensor input 712 and then send the information to an external communication device 720 which transmits this information to an external control device 716. The processor 708 may also process the information prior to sending it to the external communication device 720.

In one embodiment, the external control device 716 may have a similar internal makeup as the controller 700. For example, the external control device 716 may comprise a processor, memory, external communication device, and sensor input. Thus, the external control device 716 may receive information from sensors, other devices, or other sources. When operating, the external control device 716 may perform some or all of the processing ordinarily done by the controller's 700 processor 708 or may supplement the processed output of the processor 708 through bi-directional communication with the processor 708. In addition, the external control device 716 may perform diagnostics on the controller 700, or record and/or relay information it receives to medical personnel for treatment purposes. In one or more embodiments the external control device 716 may be a computer.

The transmission of information can be a bi-directional communication link 718 with the external control device 716 such as by way of wireless connection such as radio transmission, microwave radio transmission (telemetry), and radio frequency identification methods. Alternately, the bi-directional communication link 718 may be effectuated by a direct connection with the external control device 716 such as by an externally accessible electro-mechanical connector.

Once the information is received by the external control device 716, the information may be evaluated and data may be transmitted back to the processor 708 via the bi-directional communication link 718. In one embodiment, the data causes processor 708 to signal the restrictor driver 714 to adjust the stenosis restrictor as necessary to achieve the desired flow rate and pressure. However, the processor 708 may further process the data prior to signaling the restrictor driver 714.

The above embodiment provides a bypass graft flow control system that may continuously or periodically monitor and adjust the flow rate through the vascular bypass graft and venous outflow limb in real-time. In this embodiment, the controller monitors the flow rates in the graft and adjusts the magnitude of the stenosis restrictor to thereby maintain or modulate the flow rate which in turn will reduce clotting.

It is also contemplated that the flow through the vascular bypass graft may be controlled in a time-variant manner. The controller may be configured to selectively open and close, to any degree, the stenosis restrictor at predetermined time intervals to purge or clear the vascular bypass graft of lingering low velocity blood flow thereby reducing or inhibiting blood clots. Additionally, alternative embodiments may purge or clear the vascular bypass graft whenever a sufficiently low velocity blood flow is detected.

It is contemplated that another variation of the vascular bypass graft disclosed herein is configured with a fixed stenosis restriction. In this variation, the blood flow restriction in the venous outflow limb is non-adjustable. Thus, the proper flow rate through the vascular bypass graft would be determined and configured during its manufacture or when placed in a patient. Multiple different vascular bypass grafts of differing fixed flow rates can produced with the vascular bypass graft of proper fixed flow rate selected for a particular patient prior to surgical placement. This embodiment reduces manufacturing complexity and cost while maintaining the vascular bypass graft's resistance to occlusion by clotting.

In one or more embodiments, the vascular bypass graft 100 may be formed with a vascular connector 804, such as shown in FIGS. 8A-8D. In this manner, rather than having a venous outflow limb 106 and primary graft 105 various lumen may be attached to the vascular connector 804 to form such structures. For example, a patient's native veins could be attached to the vascular connector 804 to form a venous outflow limb 106, a primary graft 105, or both. The advantages as described above would also be present in these embodiments of the vascular bypass graft. The vascular connector 804 is beneficial in that it allows more of the vascular bypass graft 100 to be formed from a native veins, which generally have improved patency as compared to synthetic lumen. Other natural lumen could be used with the vascular connector 804 as well. For example, a vein grown in a laboratory could be used to form the primary graft 105, venous outflow limb 106 or both.

Figure 8A:
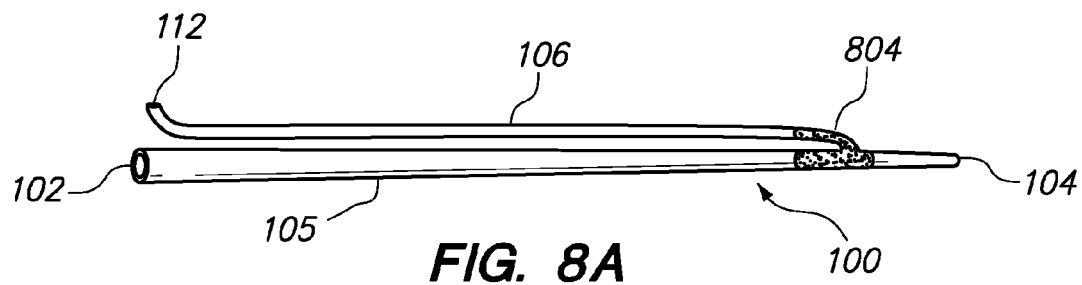
FIGS. 8A through 8D illustrate a series of alternate embodiments of a vascular connector.

FIGS. 8A-8D show various configurations of a vascular connector 804. In FIG. 8A, the vascular connector 804 is configured as a branch point from which the venous outflow limb 106 may extend from the primary graft 105. This configuration provides the benefit of providing a connector 804 which may connect to native or synthetic vessels, collectively 106, 105, 104 as determined by the treating physician and the condition of the patient.

Figure 8B:

FIG. 8B illustrates an embodiment having an elongated vascular bypass end 104. In this embodiment, the vascular connector 804 has an elongated portion 808 at the vascular bypass end 104 for connecting to the vascular system. One benefit to this configuration is that the elongated portion 808 is part of the connector 804 which decreases the time required to attach the connector to the patient.

Figure 8C:
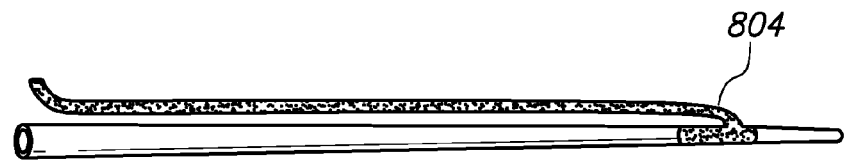
Figure 8D:
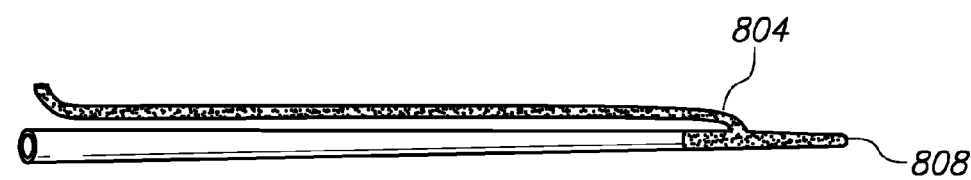

FIG. 8C illustrates an embodiment where the venous outflow limb 106 is part of the vascular connector 804. In such an embodiment, a native vessel may be used for the primary graft 105. This provides the benefit of allowing greater use of the patient's native vessel, which reduces the chance of clotting. FIG. 8D illustrates an embodiment similar to FIG. 8C having an elongated portion 808 which creates an elongated vascular bypass end 104.

Figure 9A:
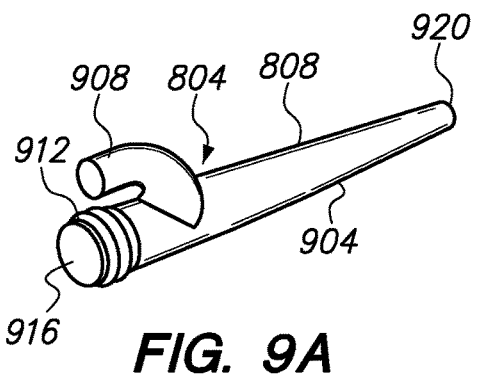
FIGS. 9A, 9B and 9C illustrate exemplary embodiments of a vascular connector.
Figure 9B:
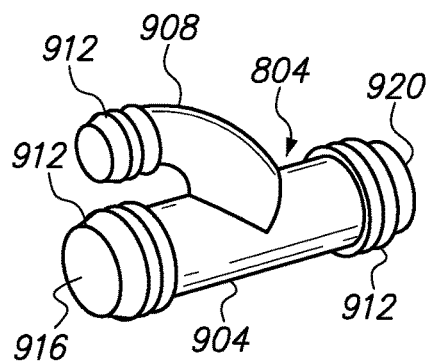
Figure 9C:
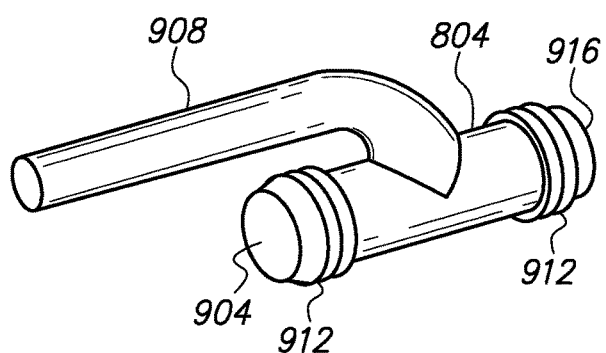

Further details regarding the vascular connector will now be disclosed with regard to FIGS. 9A-9C. As can be seen, the vascular connector 804 may comprise a venous outflow stem 908 and a primary graft stem 904. The venous outflow stem 908 may extend from the primary graft stem 904. For example, the venous outflow stem 908 may extend from an opening in the side or a wall of the primary graft stem 904. An outflow end of the venous outflow stem 908 remote from the primary graft stem 904, may connect to the vascular connector 804 to a venous outflow limb, which may be a native vessel, synthetic lumen, animal lumen, grown lumen, or other lumen. Referring to FIG. 9C, it can be seen that the venous outflow stem 908 may have an elongated shape, such as to form part of or all of a venous outflow limb. It is noted that the venous outflow stem 908 may be a separate tubular structure attached to the primary stem 904, or may be integrally formed as an extension from the tubular structure of the primary stem.

The primary graft stem 904 may be used to connect a primary graft (105, FIG. 8A) to the vascular connector 804. For example, a vein or other natural or synthetic lumen could be connected to the vascular connector such as at end 916 or 920 via the primary graft stem 904. Typically, the primary graft stem 904 will have a larger diameter than the venous outflow stem 908 so as to produce the blood flow dynamics described above. Namely, to direct blood flow primarily through the primary graft stem 904 while diverting a portion of the blood flow through the venous outflow stem 908. This ensures an adequate blood flow through the vascular connector to prevent clots and improve the patency of the vascular connector. As can be seen from FIG. 9A, the primary graft stem 904 may be tapered to adjust the blood flow though the vascular connector 804. For example, to reduce the blood flow out of the vascular connector 804 an outflow end 920 of the vascular connector may be formed with a reduced diameter.

The primary graft stem 904 may have a first end and a second end through which blood may flow. For example, as shown, the vascular connector 804 has a first vascular bypass end 916 and a second vascular bypass end 920. In general, the primary graft stem 904 will form at least part of a conduit or lumen which is used to bypass a blockage in the vascular system. To illustrate, in one embodiment, the first vascular bypass end 916 may be connected upstream of a clot or other blockage while the second vascular bypass end 920 may be connected downstream of the blockage (or vice versa). The blockage is thus bypassed in this manner. It is contemplated that one or more natural or synthetic lumen could be connected to the first or second vascular bypass ends 916,920 or both. In one or more embodiments a "bridging" lumen could be used. For example, a synthetic (or other lumen) may be used to bridge a distance between the first or second vascular bypass end 916,920 and the vascular system. The step of connecting may comprise stitching, clamping, or friction fitting or any other means for connecting known in the art or developed in the future.

It is contemplated that the vascular connector 804 may have one or more textured portions or raised portions to facilitate connections with various lumen. For example, as shown, the vascular connector 804 comprises a set of angled ridges 912 configured to allow the ends of the vascular connector to enter a lumen and to hold the vascular connector in position once inserted. For instance, the angle of the ridges 912 aids in insertion of the vascular connector 804 but resists or restricts removal of the vascular connector. This helps secure the vascular connector 804 to a lumen. As can be seen, the ridges 912 may be at one or more ends of the vascular connector 804. FIG. 9A shows the ridges 912 only at one end 916 of the primary graft stem 904 for example. FIG. 9B shows ridges 912 at each end 916,920 of the primary graft stem 904 as well as at the end of the vascular outflow stem 908, while FIG. 9C shows ridges 912 only at the ends 916,920 of the primary graft stem 904.

The vascular connector 804 may be implanted in various ways. In general, the venous outflow stem 908 will be connected to a vessel of lower pressure. Such connection may be made through one or more lumen connected to the venous outflow stem 908. The primary graft stem 904 may be connected in a similar fashion. Namely, the first and second ends 916,920 of the primary graft stem 904 may be connected to a vein or artery directly or through one or more lumen. As stated, one end of the primary graft stem 904 will typically be upstream from a blockage while the other is downstream from the blockage so as to bypass the blockage. In one or more embodiments, the ends 916, 920 of the primary graft stem 904 may be connected to an artery while the venous outflow stem 908 is connected to a vein, such as described above.

The vascular connector 804 is also beneficial in that it may be a relatively compact size and thus potentially more easily implantable in patients. In addition, the compact size allows the vascular connector 804 to be formed from rigid material if desired. The rigid material may be more durable and may be more consistent in providing a desired pressure since it is less likely to deform than a non-rigid material.

It is also contemplated the interior of the vascular connector or connecting native or synthetic vessels, collectively 106, 105, 104 may be lined with a substance or coating that resists clotting or rejection. For example, Allograft is a graft of tissue obtained from a donor of the same species as, but with a different genetic make-up from, the recipient, as a tissue transplant between two humans. This may also be called homograft. Xenograft is a graft in which the donor and recipient are of different species. An example is a vein harvested from a pig, or other animal, then used in a human. Bioengineered tissues is tissue that is grown in the lab using cells from humans or animals that can be used to create organs, skin and vessels. Drug eluting materials and chemicals may be embedded into a medical device that slowly releases a drug to block cell proliferation. This prevents fibrosis that, together with clots (thrombus), could otherwise block the artery, a process called restenosis It will be understood that the above described arrangements of apparatus and the method therefrom are merely illustrative of applications of the principles of this invention and many other embodiments and modifications may be made without departing from the spirit and scope of the invention as defined in the claims.

What is claimed is:

1. A vascular connector comprising:
   a primary stem fabricated from a substantially hollow structure and having a first end and a second end, the primary stem configured to externally connect to the primary stem to accept a blood flow from a narrowed vessel at the first end to bypass the narrowed vessel and output at least a first portion of the blood flow out the second end, the second end configured to externally connect to the narrowed vessel; and
   a secondary stem fabricated from a substantially hollow structure having a narrower diameter than the primary stem, the secondary stem extending from a wall of the primary stem to create a fluid path from the primary stem to the secondary stem and then extend linearly in a direction toward the first end of the primary stem, the secondary stem further having an outflow end configured to externally connect to a second vessel to thereby divert a second portion of the blood flow into the primary stem to the second vessel.

2. The vascular connector of claim 1 wherein at least one end of the primary stem is tapered.

3. The vascular connector of claim 1 wherein the secondary stem is integrally formed with the primary stem.

4. The vascular connector of claim 1 further comprising one or more ridges at one or both ends of the primary stem.

5. The vascular connector of claim 1 further comprising one or more ridges at an outflow end of the secondary stem.

6. The vascular connector of claim 1 further comprising a tubular venous outflow limb connected to an outflow end of the secondary stem.

7. The vascular connector of claim 1 wherein the secondary stem extends from a central portion of the primary stem.

8. The vascular connector of claim 1 wherein the secondary stem extends from a wall of the primary stem at one end of the primary stem.

9. A vascular connector comprising:
   a primary stem fabricated from a substantially hollow structure and having a first end and a second end, the primary stem configured to accept a blood flow from a narrowed vessel at the first end to bypass the narrowed vessel and output at least a first portion of the blood flow out the second end; and
   a secondary stem fabricated from a substantially hollow structure having a narrower diameter than the primary stem, the secondary stem extending from a wall of the primary stem at the second end of the primary stem to create a fluid path from the second end of the primary stem to the secondary stem, the secondary stem further having an outflow end configured to connect to a second vessel to thereby divert a second portion of the blood flow into the primary stem to the second vessel.

10. The vascular connector of claim 9 wherein the outflow end of the secondary stem has an opening that is aligned generally perpendicular to the linear direction of the primary stem.

* * * * *